(12) United States Patent
Kato

(10) Patent No.: US 6,979,337 B2
(45) Date of Patent: Dec. 27, 2005

(54) INSTRUMENT FOR EXTROVERTING BLOOD VESSEL

(75) Inventor: Yukitoshi Kato, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/993,633

(22) Filed: Nov. 27, 2001

(65) Prior Publication Data

US 2002/0065527 A1 May 30, 2002

(30) Foreign Application Priority Data

Nov. 27, 2000 (JP) .............................. 2000-359422
Mar. 14, 2001 (JP) .............................. 2001-072750

(51) Int. Cl.⁷ ............................................ A61B 17/04
(52) U.S. Cl. ..................................... 606/149; 604/271
(58) Field of Search ............................... 606/149, 153, 606/151, 155, 156, 113, 210, 211; 604/271; 600/208, 209

(56) References Cited

U.S. PATENT DOCUMENTS

| 2,940,452 A | | 6/1960 | Smialowski |
| 4,470,415 A | * | 9/1984 | Wozniak .................... 606/149 |
| 4,622,970 A | * | 11/1986 | Wozniak .................... 606/149 |
| 4,654,028 A | | 3/1987 | Suma |
| 4,762,127 A | | 8/1988 | Narayanan et al. |
| 4,917,087 A | * | 4/1990 | Walsh et al. ............... 606/153 |
| 5,486,187 A | * | 1/1996 | Schenck .................... 606/153 |
| 5,941,896 A | * | 8/1999 | Kerr .......................... 606/200 |
| 6,488,692 B1 | * | 12/2002 | Spence et al. ............. 606/153 |
| 6,569,178 B1 | * | 5/2003 | Miyawaki et al. ......... 606/169 |

FOREIGN PATENT DOCUMENTS

JP 1-43057 Y2 12/1989
WO WO 99/65409 A1 12/1999

* cited by examiner

*Primary Examiner*—Julian W. Woo
*Assistant Examiner*—Victor X Nguyen
(74) *Attorney, Agent, or Firm*—Burns, Doane, Swecker & Mathis, LLP

(57) ABSTRACT

A blood vessel extroverting instrument used to turn an end of a blood vessel inside out. The instrument has a contact portion to be brought into contact with an end of a blood vessel, a supporting portion on which the contact portion is supported, and an operating mechanism for increasing and reducing the diameter of the contact portion. At least two portions of the end of the blood vessel in the radial direction can be simultaneously expanded and/or reversed by operating the operating mechanism. Therefore the blood vessel extroverting instrument provided by the present invention is capable of easily turning an end of a blood vessel inside out in a short time without damaging the blood vessel.

15 Claims, 6 Drawing Sheets

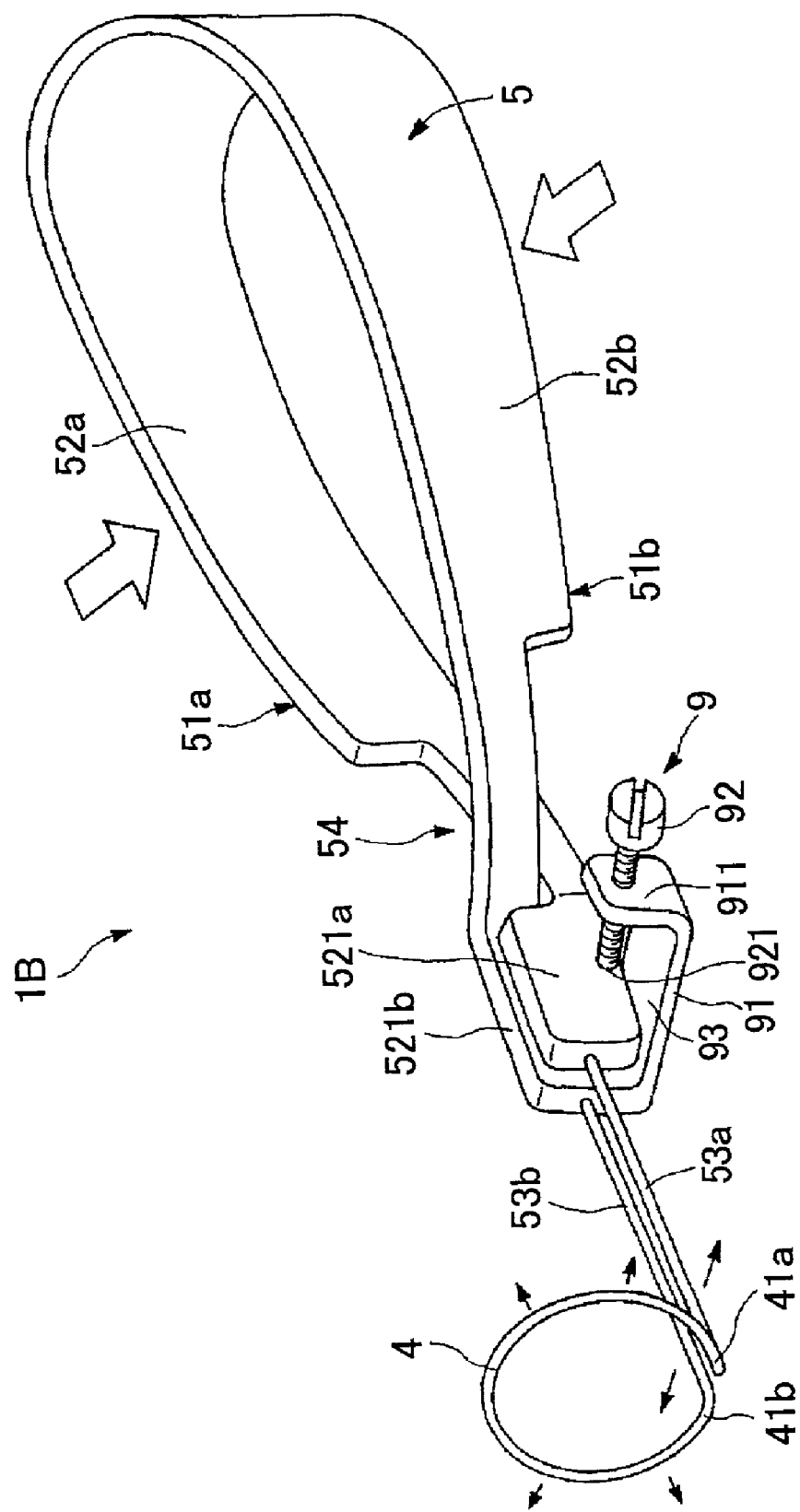

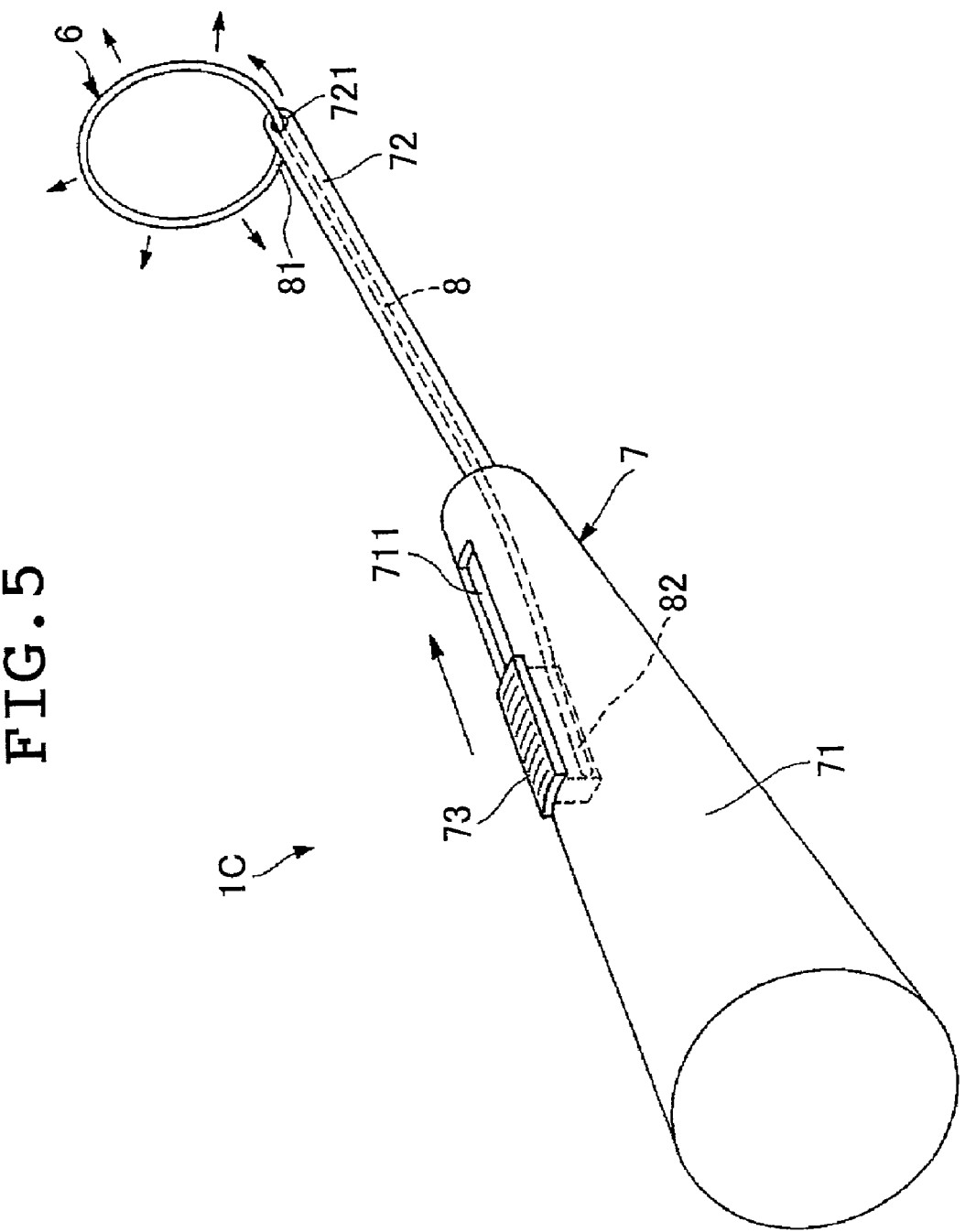

INSTRUMENT FOR EXTROVERTING BLOOD VESSEL

BACKGROUND OF THE INVENTION

The present invention relates to a blood vessel extroverting instrument used to turn an end of a blood vessel inside out.

In the field of surgery, a method of connecting ends of two blood vessels or an end and a side portion of two blood vessels by using a clip in the form of a ring (hereinafter referred to as "clip ring") as well as suture ordinarily performed is known as a method of anastomosis of blood vessels. Anastomosis using such a clip ring attracts attention because of its potential for reducing the time required for a manual procedure, and because it can be performed with no possibility of some material (e.g., a suture) other than the endothelium of a blood vessel contacting the bloodstream in the blood vessel and, hence, no risk of formation of a thrombus.

In anastomosis using a clip ring, there is a need to turn inside out (extrovert) an end of a blood vessel inserted in a clip ring. Conventionally, this extroverting operation is performed by using a method of passing a string through several places in an end portion of a blood vessel and pulling the string or a method of turning an end of a blood vessel by pinching it between tweezers.

The above-described conventional methods, however, require a high degree of handling skill and a long time to complete extroversion and entail a risk of easily damaging an end of a blood vessel.

SUMMARY OF THE INVENTION

In view of the above-described problems, an object of the present invention is to provide a blood vessel extroverting instrument with which an operator can easily perform extroversion operation of a blood vessel in a short time without damaging the blood vessel.

The above-mentioned object can be achieved by the present invention described in the following items (1) to (15).

(1) A blood vessel extroverting instrument used to turn an end of a blood vessel inside out, the instrument including: a contact portion to be brought into contact with an end of a blood vessel; a supporting portion on which the contact portion is supported; and an operating mechanism for increasing and reducing the diameter of the contact portion, wherein at least two portions of the end of the blood vessel in the radial direction can be simultaneously expanded and/or reversed by operating the operating mechanism.

(2) A blood vessel extroverting instrument as described in the above item (1), characterized in that the contact portion includes a ring portion formed of a wire-like member in the form of a substantially circular ring, the ring portion being supported on the supporting portion, the operating mechanism increasing and reducing the diameter of the ring portion, and that the ring portion is inserted into the blood vessel through the opening of the end of the blood vessel while being maintained in the state of having its diameter reduced, and the diameter of the ring portion is thereafter increased.

(3) A blood vessel extroverting instrument as described in the above item (2), characterized in that the supporting portion has a pair of arms; the wire-like member forming the ring portion is connected to distal ends of the arms; and the diameter of said ring portion is changed by changing the distance between the distal ends of the pair of arms.

(4) A blood vessel extroverting instrument as described in the above item (3), characterized in that the wire-like member or the pair of arms include intermediate portions intersecting each other.

(5) A blood vessel extroverting instrument as described in the above item (2), characterized in that the diameter of the ring portion is changed by changing the length of the wire-like member forming the ring portion.

(6) A blood vessel extroverting instrument as described in the above item (5), characterized in that the length of the wire-like member is changed by causing the wire-like member to extrude from or retract into a distal end of an insertion portion on a distal end of the supporting portion.

(7) A blood vessel extroverting instrument as described in the above item (1), characterized in that the contact portion includes a bundle of wire-like members extending radially from a proximal end connected to the supporting portion toward a distal end, the bundle of wire-like members being supported on the supporting portion, the operating mechanism changing an expanded outer configuration of the bundle of wire-like members at the distal end, and that the bundle of wire-like members is inserted into the blood vessel through the opening of the end of the blood vessel while being maintained in the state of having the diameter of the expanded outer configuration at the distal end reduced, and the diameter of the outer configuration of the bundle of wire-like members at the distal end is thereafter increased.

(8) A blood vessel extroverting instrument as described in the above item (7), characterized in that the operating mechanism comprises a hollow tubular member capable of covering the periphery of the bundle of wire-like members and moving along the lengthwise direction of the bundle of wire-like members.

(9) A blood vessel extroverting instrument as described in the above item (7), characterized in that the hollow tubular member has an inside diameter smaller than the expanded outer configuration of the bundle of wire-like members at the distal end; the diameter of the expanded outer configuration of the bundle of wire-like members at the distal end is reduced by moving the hollow tubular member toward the distal end of said bundle of wire-like members; and the diameter of the expanded outer configuration of the bundle of wire-like members at the distal end is increased by moving the hollow tubular member in the direction from the distal end to the proximal end of the bundle of wire-like members.

(10) A blood vessel extroverting instrument as described in the above item (7), characterized by further including a grip portion provided at a proximal end of the supporting portion.

(11) A blood vessel extroverting instrument as described in any one of the above items (1) to (10), characterized in that the contact portion is made of an elastic material or a superelastic material.

(12) A blood vessel extroverting instrument as described in any one of the above items (1) to (11), characterized by further including regulatory means for regulating the operating mechanism.

(13) A blood vessel extroverting instrument as described in the above item (12), characterized in that the regulatory means includes an adjustment means capable of position adjustment.

(14) A blood vessel extroverting instrument as described in any one of the above items (1) to (13), characterized in that the contact portion is in the state of having its diameter reduced when said supporting portion is in an unrestrained state, and the diameter of the contact portion is increased when the supported portion is in an urged state.

(15) A set of a blood vessel extroverting instrument as described in any one of the above items (1) to (14) and a clip ring capable of being fitted around a blood vessel.

BRIEF DESCRIPTION OF THE DRAWINGS

In the accompanying drawings:

FIG. 4 is a perspective view showing a blood vessel extroverting instrument in accordance with a second embodiment of the present invention;

FIG. 5 is a perspective view showing a blood vessel extroverting instrument in accordance with a third embodiment of the present invention;

DETAILED DESCRIPTION OF THE INVENTION

A blood vessel extroverting instrument in accordance with the present invention has a contact portion to be brought into contact with an end of a blood vessel, a supporting portion on which the contact portion is supported, and an operating mechanism for changing the diameter of the contact portion. An operator can simultaneously expand and/or reverse a continuous part or at least two portions, preferably three or more portions of the end of the blood vessel in the radial direction by operating the operating mechanism.

Blood vessel extroverting instruments which represent preferred embodiments of the present invention will be described with reference to FIGS. 1 through 8. However, the blood vessel extroverting instrument of the present invention is not limited to the embodiments described below.

<First Embodiment>

Figure 1:
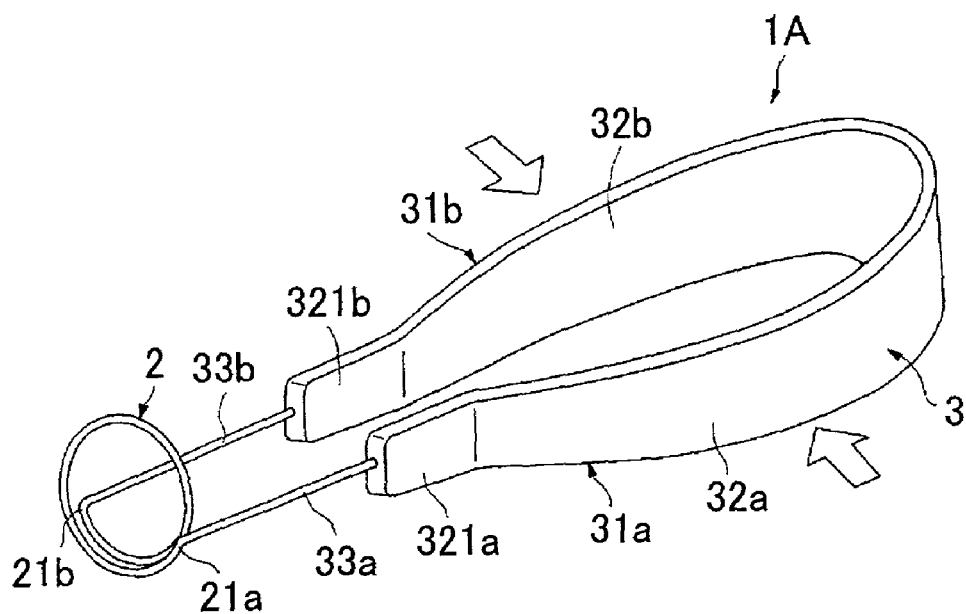
FIG. 1 is a perspective view showing a blood vessel extroverting instrument in accordance with a first embodiment of the present invention (in a state where the diameter of a ring portion is reduced)
Figure 2:
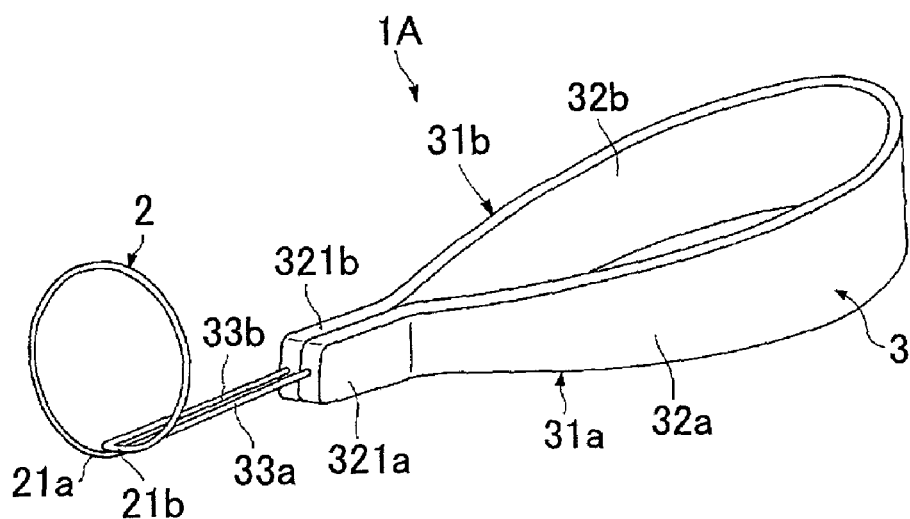
FIG. 2 is a perspective view showing the blood vessel extroverting instrument in accordance with the first embodiment of the present invention (in a state where the diameter of a ring portion is increased)
Figure 3A:
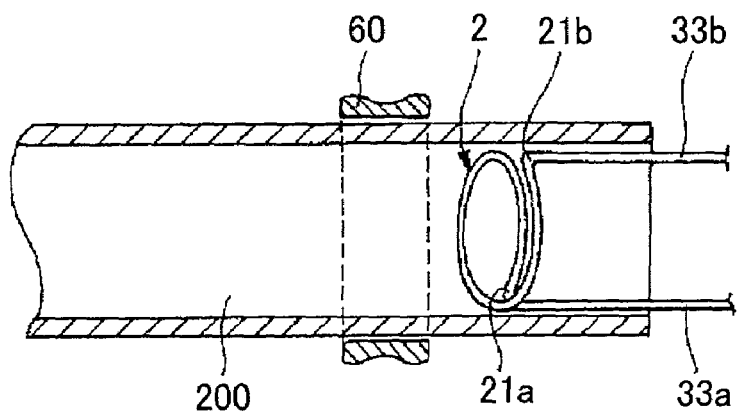
FIGS. 3A, 3B, and 3C are longitudinal sectional views of the blood vessel extroverting instrument shown in FIG. 1, for showing a sequence of steps in the method of using the instrument.
Figure 3B:
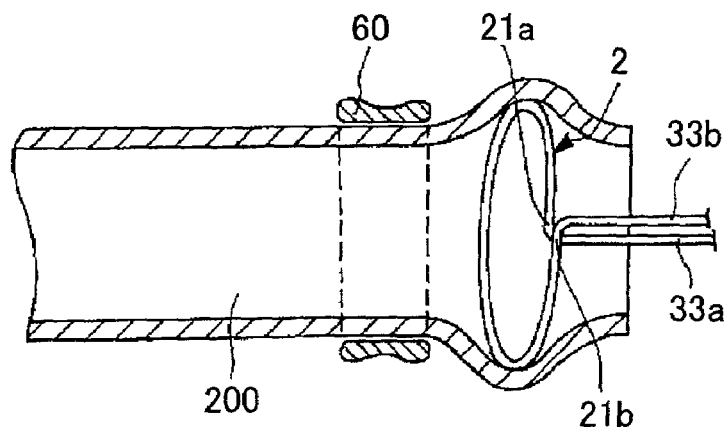
Figure 3C:
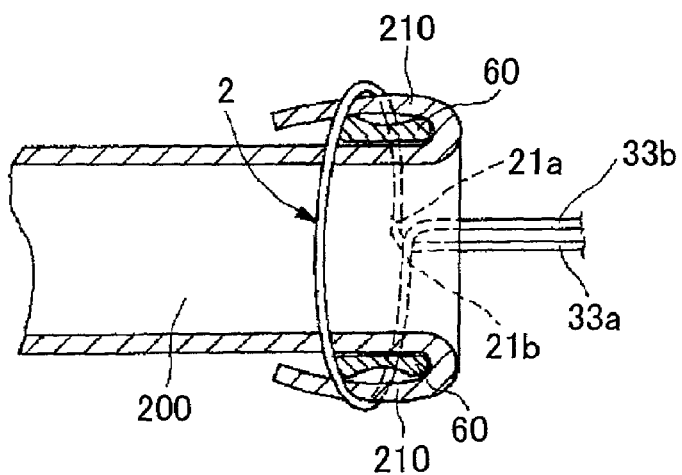

FIGS. 1 and 2 are perspective views of the blood vessel extroverting instrument in accordance with the first embodiment of the present invention, respectively showing a state where the diameter of a ring portion is reduced and a state where the diameter of the ring portion is increased. FIGS. 3A, 3B, and 3C are longitudinal sectional views of the blood vessel extroverting instrument, showing a sequence of steps in the method of using the instrument. In FIGS. 1 and 2, the ring portion is shown by being exaggerated in size relative to a supporting portion for convenience sake (the corresponding portion is also illustrated in the same manner in FIGS. 4 and 5 referred to below). In the following description, the end of the blood vessel extroverting instrument on the operator's hand side will be referred to as "proximal end", the other end to be brought into contact with an end of a blood vessel when the instrument is operated will be referred to as "distal end", and the direction along which the instrument extends between the proximal end and the distal end will be referred to as "lengthwise direction".

The blood vessel extroverting instrument indicated by 1A in FIG. 1 is used to turn an end of a blood vessel inside out. The blood vessel extroverting instrument 1A has a ring portion 2, arm portions 31a and 31b, and a supporting portion 3. The ring portion 2 on the distal end is supported by the arm portions 31a and 31b of the blood vessel extroverting instrument 1A. The construction of each portion will be described below.

The ring portion 2 is a portion which can be inserted into a blood vessel through the opening at an end of the blood vessel, and which is formed by curving a wire-like member into the shape of a substantially circular ring generally parallel to a plane perpendicular to the lengthwise direction. Preferably insertion portions 33a and 33b are formed of wire-like members integrally with the ring portion 2. The insertion portions 33a and 33b extend along the lengthwise direction and support the ring portion 2 at their ends. The insertion portions 33a and 33b and the ring portion 2 connect to each other through two ends shown as one end 21a and the other end 21b.

The wire-like member for forming the ring portion 2 is doubly formed as a part of the ring portion 2 (substantially as a lower half of the ring portion 2 as viewed in FIG. 1). That is, opposite end portions of the wire-like member forming the ring portion 2 are in a state of intersecting each other.

Preferably, the outer diameter of the ring portion 2 is ordinarily about 1 to 20 mm in the most contracted state, depending upon the diameter of a blood vessel to be extroverted.

It is also preferred that the outer diameter of the ring portion 2 when reduced to the smallest value with respect to a blood vessel to be extroverted should be substantially equal to or smaller than the inside diameter of the blood vessel, and that the inside diameter of the ring portion 2 when expanded to the largest value should be larger than the value of {(the outer diameter of the blood vessel)+(the thickness of the blood vessel)×2}.

No particular limitation is imposed on selection of the material for the thus-formed ring portion 2. For example, the material for the ring portion 2 is selected from various metallic materials, such as stainless steel, aluminum and an aluminum alloy, titanium and a titanium alloy, and a nickel-titanium alloy, or from various resin materials.

Among such materials, a material substantially elastic in the range of deformation caused during use of the blood vessel extroverting instrument 1A, for example, a superelastic material (superelastic alloy) such as a nickel-titanium alloy is preferred for the ring portion 2. If the ring portion 2 is formed of such a superelastic alloy, its shape close to a circle (perfect circle) can be maintained even when the ring portion 2 is deformed by being changed in diameter. Also, the ring portion 2 formed of such a superelastic alloy has improved durability.

No particular limitation is imposed on selection of the cross-sectional shape of the wire-like member forming the ring portion 2. However, a shape having substantially no angular portion, e.g., a circle or an ellipse is preferred as the cross-sectional shape of the wire-like member. Preferably, the thickness (width) of the wire-like member forming the ring portion 2 is ordinarily about 0.1 to 2.0 mm, depending upon the kind and the thickness of a blood vessel to be extroverted and other factors.

The supporting portion 3 on which the ring portion 2 is supported has a pair of arm portions 31a and 31b. The arm portion 31a is constituted by a grip portion 32a in the form of a plate, an end 321a of the same and the insertion portion 33a fixed to the end 321a of the grip portion 32a. Similarly, the arm portion 31b is constituted by a grip portion 32b in the form of a plate, an end 321b of the same and the insertion portion 33b fixed to the grip portion 32b.

The insertion portions 33a and 33b can be inserted into a blood vessel through the opening at an end of the blood vessel together with the ring portion 2. The insertion portions 33a and 33b are provided in a state of projecting respectively from the ends 321a and 321b of the grip portions 32a and 32b to the distal end of the instrument. The ring portions 2 are connected to the insertion portions 33a and 33b through one end 21a and the other end 21b at the distal ends of the insertion portions 33a and 33b. In this embodiment, the insertion portions 33a and 33b are formed by the same wire-like member as that of the ring portion 2 continuously through one end 21a and the other end 21b.

Proximal ends of the grip portions 32a and 32b are connected to each other. For example, the grip portions 32a and 32b are formed by bending (curving) a central portion of a member in the form of a plate made of a metallic material such as stainless steel or a material selected from various resin materials, etc.

Preferably, the grip portions 32a and 32b have resiliency such as to be capable of maintaining their ends 321a and 321b in a state of being spaced apart from each other (an open state) when the grip portions 32a and 32b are in an unrestrained state. In this embodiment, the ring portion 2 can be automatically returned from a large-diameter state to a small-diameter state by the urging force of the grip portions 32a and 32b. Therefore the instrument has improved operability.

In the thus-constructed blood vessel extroverting instrument 1A in the unrestrained state, each of the pair of ends 321a and 321b of the grip portions 32a and 32b, the pair of insertion portions 33a and 33b and the pair of the opposite ends (one end 21a and the other end 21b) of the wire-like member forming the ring portion 2 are positioned apart from each other and the ring portion 2 is in a small-diameter state, as shown in FIG. 1.

The operating mechanism for changing the diameter of the ring portion will now be described. The grip portions 32a and 32b are operated by, for example, being gripped in an operator's hand when the ring portion is in the small-diameter state. A force is thereby applied in the direction indicated by outlined arrows in FIG. 1 to bring each of the pair of ends 321a and 321b of the grip portions 32a and 32b, the pair of insertion portions 33a and 33b and the pair of the opposite ends (one end 21a and the other end 21b) of the wire-like member forming the ring portion 2 closer to each other. The diameter of the ring portion 2 is thereby increased.

The blood vessel extroverting instrument 1A of this embodiment may have a regulating means for regulating the maximum diameter (size) of the ring portion 2. That is, as shown in FIG. 2, the diameter of the ring portion 2 is maximized when the ends 321a and 321b of the grip portions 32a and 32b are brought into contact with each other. Thus, the diameter of the ring portion 2 is regulated so as not to increase further. The maximum diameter of the ring portion 2 is set to a value large enough to extrovert a blood vessel. The limiting means is used to prevent a blood vessel from being excessively expanded to be damaged. It is preferable to use the limiting means because of this effect of improving safety.

When the grip portions 32a and 32b are released from the state in operation shown in FIG. 2, i.e., from a grip in a hand or the like, they return to the state shown in FIG. 1 by their resiliency and/or the resiliency of the ring portion 2.

In the present invention, a mechanism capable of fixing the diameter (size) of the ring portion 2 at an arbitrary or predetermined size may be provided. The operability is thereby improved. In this embodiment, such a fixing mechanism is constituted by, for example, a regulatory means for regulating the distance between the ends of both the grip portions 32a and 32b.

An example of the method of using the blood vessel extroverting instrument 1A (the operation of the instrument) will next be described in detail.

(1) As shown in FIG. 3A, an end of a blood vessel 200 is passed through a clip ring 60, and the distal end (ring portion 2, insertion portions 33a and 33b) of the blood vessel extroverting instrument 1A is inserted into the blood vessel 200 through the end opening of the blood vessel 200. When this insertion is performed, the ring portion 2 is maintained in the small-diameter state (the state shown in FIG. 1). This operation is performed while the clip ring 60 is supported by, for example, being pinched between tweezers (not shown). The clip ring 60 is not exclusively used if the blood vessel can be fixed by using, instead of the clip ring 60, a divisible pipe-shaped instrument which can be removed after the completion of extroversion, a pair of tweezers, or the like.

(2) Next, as shown in FIG. 3B, the grip portions 32a and 32b are operated by, for example, being gripped in a hand to set the ring portion 2 in the large-diameter state (the state shown in FIG. 2). The portion of the blood vessel 200 positioned around the ring portion 2 is thereby expanded outward. During this operation in this embodiment, one end 21a and the other end 21b can be brought closer to each other by gripping the grip portions 32a and 32b in a hand to increase the diameter of the ring portion 2. Thus, the instrument has improved operability.

(3) Thereafter, the ring portion 2 is brought closer to the clip ring 60 (or the clip ring 60 is brought closer to the ring portion 2) to insert the clip ring 60 into a position inside the ring portion 2 with the increased diameter. A portion of the blood vessel 200 at the end of the same is thereby turned inside out to form a turned portion 210, with which the outer periphery of the clipping 60 is covered, as shown in FIG. 3C. The ring portion 2 is then removed from the blood vessel 200 to complete the extroverting operation.

<Second Embodiment>

FIG. 4 is a perspective view showing a blood vessel extroverting instrument in accordance with a second embodiment of the present invention.

The blood vessel extroverting instrument of this embodiment will be described with reference to FIG. 4 mainly with respect to points of difference from the above-described embodiment. The description for the same details will not be repeated.

The blood vessel extroverting instrument 1B shown in FIG. 4 is used to turn an end of a blood vessel inside out, as is the blood vessel extroverting instrument 1A, and has a ring portion 4 positioned at its distal end, arm portions 51a and 51b for supporting the ring portion 2, and a supporting portion 5. The construction of each portion will be described below.

The ring portion 4 is a portion which can be inserted into a blood vessel through the opening at an end of the blood vessel, and which is formed by curving a wire-like member into the shape of a substantially circular ring generally parallel to a plane perpendicular to the lengthwise direction. Preferably insertion portions 53a and 53b are formed of wire-like members integrally with the ring portion 4. The insertion portions 53a and 53b extend along the lengthwise direction and support the ring portion 4 at their ends. The insertion portions 53a and 53b and the ring portion 4 connect to each other through two ends shown as one end 41a and the other end 41b.

The ring portion 4 includes no doubly-formed portions (intersecting portions) of the above-described wire-like member. One end 41a and the other end 41b of the wire-like member forming the ring portion 4 are positioned respectively at lower positions of the ring portion 4 as viewed in FIG. 4.

The supporting portion 5 on which the ring portion 4 is supported has a pair of arm portions 51a and 51b. The arm portion 51a is constituted by a grip portion 52a in the form of a plate, an end 521a of the same and the insertion portion 53a fixed to the end 521a of the grip portion 52a. Similarly, the arm portion 51b is constituted by a grip portion 52b in the form of a plate, an end 521b of the same and the insertion portion 53b fixed to the end 521b of the grip portion 52b.

Proximal ends of the grip portions 52a and 52b are connected to each other. The grip portions 52a and 52b are formed by bending (curving) a central portion of a member in the form of a plate made of a metallic material such as stainless steel or a material selected from various resin materials, etc.

The grip portions 52a and 52b include intersecting portions 54 formed at intermediate positions thereof so as to intersect the grip portions 52a and 52b with each other. The distal end of the grip portion 52a is on the left-hand side of the distal end of the grip portion 52b. Conversely, the proximal end of the grip portion 52b is on the right-hand side of the proximal end of the grip portion 52b.

Preferably, the thus-formed grip portions 52a and 52b have resiliency such as to be capable of maintaining their ends 521a and 521b in a state of being in contact with or close to each other (a closed state) in an unrestrained state.

The insertion portions 53a and 53b are provided in a state of projecting respectively from the ends 521a and 521b of the grip portions 52a and 52b to the distal end of the instrument. The ring portion 4 is connected to the insertion portions 53a and 53b through one end 41a and the other end 41b at the distal ends of the insertion portions 53a and 53b.

In the thus-constructed blood vessel extroverting instrument 1B in the unrestrained state, each of the pair of ends 521a and 521b of the grip portions 52a and 52b, the pair of insertion portions 53a and 53b and the pair of the opposite ends (one end 41a and the other end 41b) of the wire-like member forming the ring 4 are in contact with or close to each other and the ring portion 4 is in a small-diameter state, as shown in FIG. 4.

The operating mechanism for changing the diameter of the ring portion will now be described. The grip portions 52a and 52b are operated by, for example, being gripped in an operator's hand when the ring portion is in the small-diameter state. A force is thereby applied as indicated by outlined arrows in FIG. 4 to move each of the pair of ends 521a and 521b of the grip portions 52a and 52b, the pair of insertion portions 53a and 53b and the pair of the opposite ends (one end 41a and the other end 41b) of the wire-like member forming the ring portion 4 apart from each other. The diameter of the ring portion 4 is increased to make the ring portion 4 into C-shape. When the gripping force to the grip portions 52a and 52b is removed, the grip portions 52a and 52b return to the state shown in FIG. 4 by their resiliency (or by their resiliency and the resiliency of the ring portion 4).

The blood vessel extroverting instrument 1B of this embodiment may have a regulatory means 9 for regulating the maximum diameter (size) of the ring portion 4. It is preferable to provide the limiting means 9 because it enables adjustment of the maximum diameter (size) of the ring portion 4.

The limiting means 9 is preferably constituted by a hook 91 formed so as to project from the end 521b of the grip portion 52b to a position outside the other end 521a, and a stopper 92 formed of a threaded member screwed into a side plate 911 of the hook 91.

The side plate 911 of the hook 91 is formed substantially parallel to the ends 521a and 521b of the grip portions 52a and 52b. The end 521a of the grip portion 52a is inserted in a channel 93 formed between the end 521b and the side plate 911.

The limiting means 9 thus provided stops the ends 521a and 521b of the grip portions 52a and 52b from being moved away from each other when the outer surface of the end 521a of the grip portion 52a is brought into contact with an end 921 of the stopper 92. The maximum diameter (size) of the ring portion 4 is determined in correspondence with this state. This limiting means prevents a blood vessel from being excessively expanded to be damaged, as does that in the first embodiment. Thus, a further improvement in safety is achieved.

Further, it is possible to adjust the maximum diameter (size) of the ring portion 4 to a selected value through adjustment of the maximum distance between the ends 521a and 521b of the grip portions 52a and 52b, which is performed by rotating the stopper 92. The range of application of the instrument can be increased by adjusting the instrument in this manner to different thicknesses of blood vessels in various cases of diseases or regions to which the instrument is applied.

Various conditions, operations and effects relating to the diameter (size) and the material for the ring portion 4 and the thickness of the wire-like member in this blood vessel extroverting instrument 1B are the same as those in the above-described blood vessel extroverting instrument 1A.

<Third Embodiment>

FIG. 5 is a perspective view of a blood vessel extroverting instrument in accordance with a third embodiment of the present invention.

The blood vessel extroverting instrument of this embodiment will be described with reference to FIG. 5 mainly with respect to points of difference from the above-described embodiments. The description for the same details will not be repeated.

The blood vessel extroverting instrument 1C of this embodiment shown in FIG. 5 is used to turn an end of a blood vessel inside out, and has a ring portion 6 positioned at its distal end and a supporting portion 7 on which the ring portion 6 is supported. The construction of each portion will be described below.

The ring portion 6 is formed by curving a portion of a wire-like member 8 into the shape of a substantially circular ring generally parallel to a plane perpendicular to the lengthwise direction.

The supporting portion 7 is constituted by a grip portion 71 which can be gripped in a hand, and an insertion portion 72 formed so as to project from an end of the grip portion 71 to the distal end of the instrument.

The insertion portion 72 is a slender tubular member (pipe) made of a material selected from various metallic materials, e.g., stainless steel, or a material selected from various resin materials, etc. The wire-like member 8 is passed through the insertion portion 72.

The passage for the wire-like member 8 formed in the insertion portion 72 is curved (bent) (to the right as viewed in FIG. 5) to form an external opening 721 at the distal end of the insertion portion 72 so that the opening 721 faces in a direction substantially perpendicular to the lengthwise direction.

A portion of the wire-like member 8 in the vicinity of the distal end of the insertion portion 72 extrudes from and retracts into the opening 721 in a direction substantially perpendicular to the lengthwise direction.

An end 81 of the wire-like member 8 extending out of the opening 721 is fixed to a side portion of the distal end of the insertion portion 72 by, for example, glueing, welding or caulking.

The portion of the wire-like member 8 between the end 81 and the opening 721 forms the ring portion 6.

An end 82 of the wire-like member 8 on the opposite side is introduced into the interior of the grip portion 71 through a proximal end of the insertion portion 72 and is connected to a slider portion positioned inside the grip portion 71 of a slider (operating portion) 73 mounted on the grip portion 71.

The slider 73 is mounted so as to be slidable through a predetermined range along the lengthwise direction in a slit 711 formed in the grip portion 71. An operator can move the slider 73 along the lengthwise direction by, for example, putting his or her thumb on a portion of the slider 73 located outside the grip portion 71.

When the slider 73 is moved relative to the grip portion 71 toward the distal end as indicated by the arrow in FIG. 5, the wire-like member 8 is paid out through the opening 721 to increase the length of the portion of the wire-like member 8 forming the ring portion 6, thereby increasing the diameter of the ring portion 6.

Conversely, when the slider 73 is moved relative to the grip portion 71 toward the proximal end, the wire-like member 8 retracts into the insertion portion 72 through the opening 721 to reduce the length of the portion of the wire-like member 8 forming the ring portion 6, thereby reducing the diameter of the ring portion 6.

The blood vessel extroverting instrument 1C of this embodiment may have a limiting means for limiting the maximum diameter (size) of the ring portion 6. That is, when the slider 73 is brought into contact with a distal end of the slit 711, the wire-like member 8 is not further paid out through the opening 721 of the insertion portion 72. In this state, therefore, the size of the ring portion 6 is maximized and the diameter of the ring portion 6 is not further increased. The regulatory means is used to prevent a blood vessel from being excessively expanded to be damaged, as is that in the above-described embodiments. It is preferable to use the regulatory means because of this effect of improving safety.

In this embodiment, it is possible to adjust the maximum diameter (size) of the ring portion 6 to a selected value by, for example, performing variable setting of the fixed position of the end (proximal end) 82 of the wire-like member 8 relative to the slider 73. The range of application of the instrument can be increased by adjusting the instrument in this manner to different thicknesses of blood vessels in various cases of diseases or regions to which the instrument is applied.

In this embodiment, the slider 73 may be urged in the direction of the proximal end or the distal end by, for example, connecting a spring (not shown) to the slider 73. In this manner, urging in the direction for setting the ring portion 6 in the small-diameter state or large-diameter state, corresponding to the manner in the above-described embodiments, can be performed.

Also, a mechanism capable of fixing the diameter (size) of the ring portion 6 at an arbitrary or predetermined size may be provided. Such a fixing mechanism is constituted by, for example, a positioning means for determining the position of the slider 73 relative to the grip portion 71.

Various conditions, operations and effects relating to the diameter (size) and the material for the ring portion 6 and the thickness of the wire-like member in this blood vessel extroverting instrument IC are the same as those described above with respect to the blood vessel extroverting instrument 1A.

<Fourth Embodiment>

Figure 6:
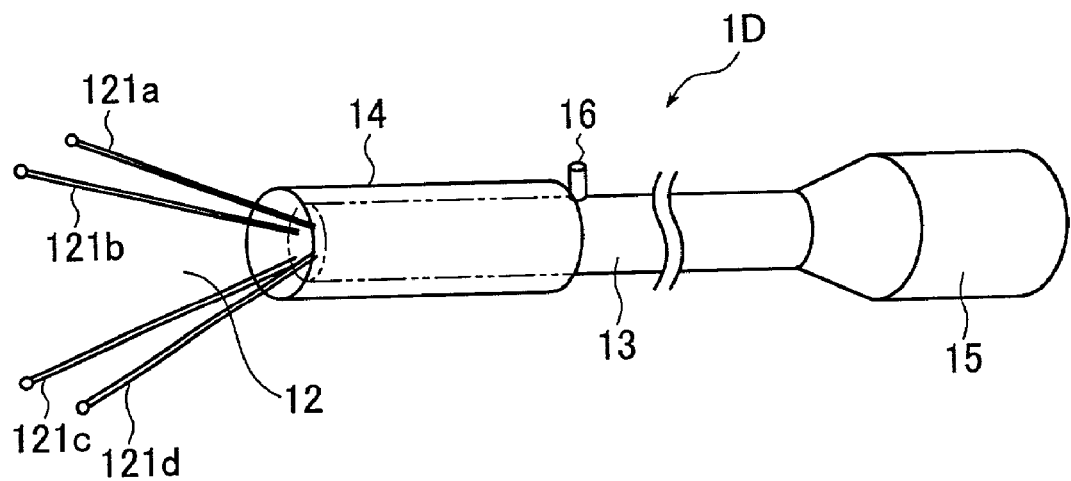
FIG. 6 is a perspective view showing a blood vessel extroverting instrument in accordance with a fourth embodiment of the present invention (in a state where the outer diameter of an expanded outer configuration of a bundle of wire-like members on a distal end is increased)
Figure 7:
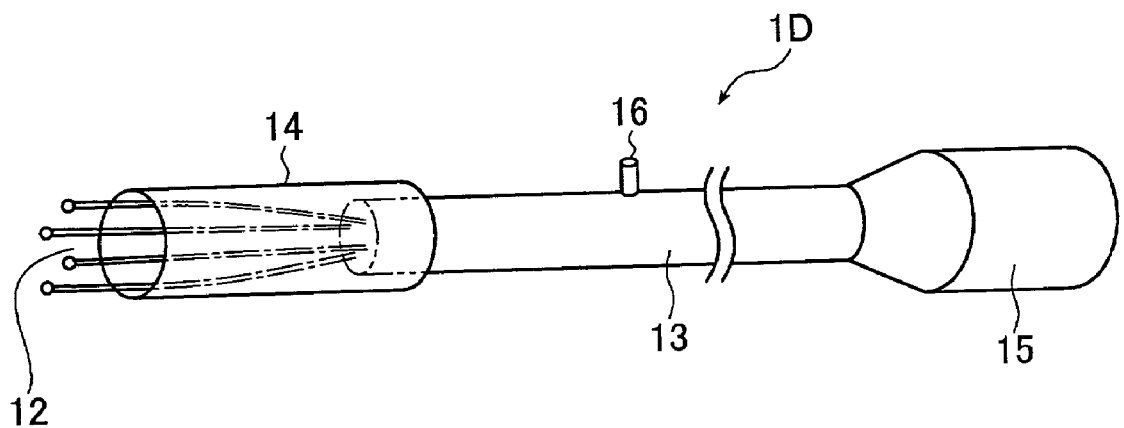
FIG. 7 is a perspective view showing the blood vessel extroverting instrument in accordance with the fourth embodiment of the present invention (in a state where the outer diameter of the expanded outer configuration of the bundle of wire-like members at the distal end is reduced)

A blood vessel extroverting instrument 1D shown in FIGS. 6 and 7 is an instrument used to turn an end of a blood vessel inside out. The blood vessel extroverting instrument 1D has a bundle of wire-like members 12 used as a member to be brought into contact with an end of a blood vessel, a supporting portion 13 on which the bundle of wire-like members 12 is supported, and a hollow member 14 which constitutes an operating mechanism for increasing and reducing the diameter of the distal end of the bundle of wire-like members 12. The blood vessel extroverting instrument 1D is an instrument capable of simultaneously expanding and/or extroverting at least two portions of an end of a blood vessel in the radial direction by operating the hollow member 14 constituting the operating mechanism.

Figure 8A:
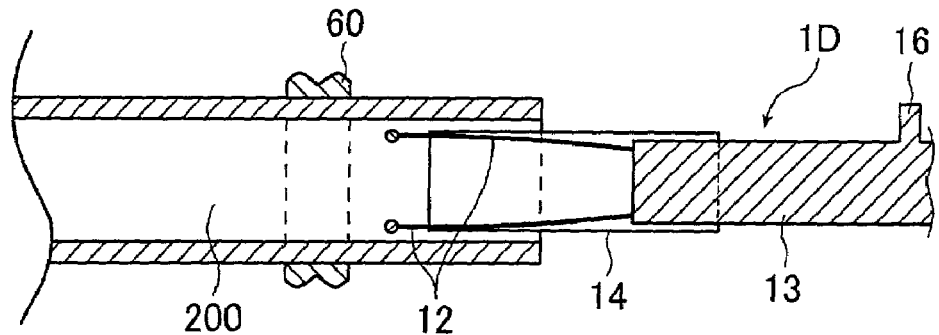
FIGS. 8A, 8B, and 8C are longitudinal sectional views of the blood vessel extroverting instrument shown in FIG. 6, for showing a sequence of steps in the method of using the instrument.
Figure 8B:
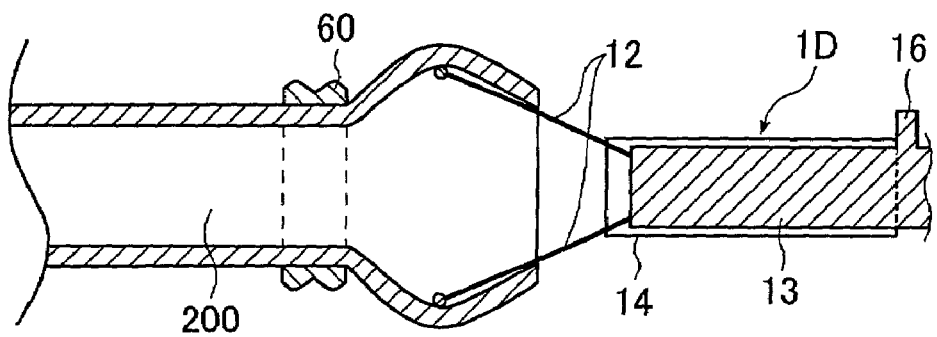
Figure 8C:
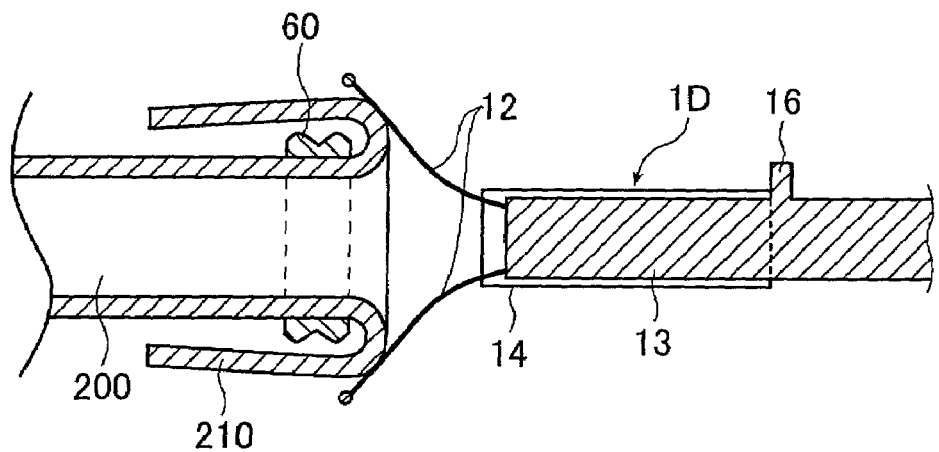

FIG. 6 is a perspective view of the blood vessel extroverting instrument in the fourth embodiment of the present invention in a state where the bundle of wire-like members 12 is expanding radially from an end of the bundle of wire-like members 12 on the proximal end side (hereinafter referred to as "proximal end") to an end of the bundle of wire-like members 12 on the distal end side (hereinafter referred to as "distal end"). FIG. 7 is a perspective view of the blood vessel extroverting instrument shown in FIG. 6, showing a state where the distal end of the bundle of wire-like members 12 is restrained by hollow member. FIGS. 8A, 8B, and 8C are longitudinal sectional views of the blood vessel extroverting instrument shown in FIG. 6, showing a sequence of steps in the method of using the instrument. In FIGS. 6 and 7, the bundle of wire-like members is shown by being exaggerated in size relative to the supporting portion for convenience sake (the bundle of wire-like members is also illustrated in the same manner in FIGS. 8A, 8B, and 8C referred to below).

The blood vessel extroverting instrument 1D shown in FIG. 6 is used to turn an end of a blood vessel inside out, and has the bundle of wire-like members 12 positioned at its distal end, the supporting portion 13 on which the bundle of wire-like members 12 is supported, and the hollow member 14 capable of covering the bundle of wire-like members 12. The construction of each component will be described below.

The bundle of wire-like members 12 is formed of two or more wire-like members. FIG. 6 illustrates a case where the bundle of wire-like members 12 is formed of four wire-like members 121a, 121b, 121c, and 121d. As shown in FIG. 6, the wire-like members 121a, 121b, 121c, and 121d are fixed on the supporting portion 13 so that the distal end of the bundle of wire-like members 12 expand radially when the bundle of wire-like members 12 is not covered with the hollow member 14.

The number of wire-like members is not particularly limited as long as the number thereof is equal to or more than two. Preferably, it is three or more. It is desirable to provided two or more wire-like members in order to ensure certain facility and safety with which the operation for extroverting a blood vessel is performed.

The placement of the wire-like members 121a, 121b, 121c, and 121d is not limited to a particular manner. However, it is preferred that the wire-like members 121a, 121b, 121c, and 121d be placed so as to have point symmetry about a center of the supporting member 13.

It is preferred that the distal ends of the wire-like members 121a, 121b, 121c, and 121d have a spherical shape, as shown in FIG. 6. Such a shape is selected in order to prevent damage to a wall portion of a blood vessel when the wire-like members are inserted into the blood vessel, as described below. To form each of the wire-like members 121a, 121b, 121c, and 121d so that the distal end has a spherical shape, the wire-like member may be worked by laser melting or a spherical member separately provided may be attached to the end of the wire-like member. Also, the distal end may have a shape other than the spherical shape if the same effect can be obtained. For example, the end of the wire-like member may be formed into the shape of a ring.

No particular limitation is imposed on selection of the material for the thus-formed wire-like members 121a, 121b, 121c, and 121d. For example, the material for the wire-like members is selected from various metallic materials, such as stainless steel, aluminum and an aluminum alloy, titanium and a titanium alloy, and a nickel-titanium alloy, or from various resin materials.

Among such materials, a material substantially elastic in the range of deformation caused during use of the instrument, for example, a superelastic material (superelastic alloy) such as a nickel-titanium alloy is preferred. If each of the wire-like members 121a, 121b, 121c, and 121d is formed of such a superelastic alloy, suitable point symmetry of the bundle of wire-like members 12 can be maintained even when the expanded outer configuration of the bundle of wire-like members 12 at the distal end is deformed by being increased and reduced in diameter. Also, the wire-like member formed of such a superelastic alloy has improved durability.

Preferably, the thickness of the wire-like members 121a, 121b, 121c, and 121d is ordinarily about 0.1 mm to about 2.0 mm, depending upon the kind and the thickness of a blood vessel to be extroverted and other factors. It is noted that the construction of the bundle of wire-like members of the present invention is not limited to wire-like shape. The bundle of strips is included in the bundle of wire-like members of the present invention, or the strip may have convex or concave section, or the wire-like members may have distal end part such as strip-like part, rod like part, convex strip-like part, or concave strip-like part.

Preferably, the supporting portion 13 on which the bundle of wire-like members 12 is supported is made of a rigid material. A material selected from various metallic materials, resin materials, etc., may be preferably used as the material for the supporting portion 13.

FIG. 7 illustrates a state where the hollow member 14 is moved toward the distal end to reduce the outer diameter of the expanded outer configuration of the bundle of wire-like members 12 at the distal end.

The inside diameter of the hollow member 14 is smaller than the outer diameter of the expanded distal end of the bundle of wire-like members 12. Preferably, the hollow member 14 is formed of a rigid pipe. A material selected from various metallic materials, resin materials, etc., may be preferably used as the material for the hollow member 14.

A regulatory member 16 is provided on the supporting member 13. The regulatory member 16 has the function of limiting the movement of the hollow member 14 in the direction from the distal end to the proximal end of the bundle of wire-like members 12 to regulate the expansion of the bundle of wire-like members 12 at the distal end.

It is desirable that the regulatory member 16 be mounted so as to be movable along the lengthwise direction of the supporting member 13 to enable adjustment of the expansion of the bundle of wire-like members 12 at the distal end according to the diameter of a blood vessel to be extroverted and to thereby prevent the blood vessel from being excessively expanded.

For example, a structure for enabling the regulatory member 16 to be mounted as described above may be realized in such a manner that the regulatory member 16 is screwed into the supporting portion 13 and a plurality of threaded holes are provided along the lengthwise direction of the supporting member 13. Alternatively, the regulatory member 16 may be fixed at an arbitrary position in a groove formed in the supporting member 13.

If the regulatory member 16 for regulating the expansion of the bundle of wire-like members is provided, a blood vessel to be extroverted is prevented from being excessively expanded, thus achieving a further improvement in safety. Further, if the adjustment mechanism for adjusting the expansion of the bundle of wire-like members is provided, the range of application of the instrument can be increased by adjusting the instrument to different diameter of blood vessels in various cases of diseases or regions to which the instrument is applied.

Also, a grip portion 15 is provided at the proximal end of the supporting portion 13 to improve the operability. The grip portion 15 may be formed integrally with the supporting portion 13 or may be provided as a separate member and fixed to the supporting portion 13.

An example of a method of using the blood vessel extroverting instrument 1D (the operation of the instrument) will next be described in detail.

(1) As shown in FIG. 8A, an end of a blood vessel 200 is passed through a clip ring 60, and the distal end (the distal end of the bundle of wire-like members 12) of the blood vessel extroverting instrument 1D is inserted into the blood vessel 200 through the end opening of the blood vessel 200. This operation is performed while the clip ring 60 is supported by, for example, being pinched between tweezers (not shown). Before this insertion, the hollow member 14 is moved toward the distal end to maintain the bundle of wire-like members 12 in the state of having the outer diameter of the distal end reduced (the state shown in FIG. 7).

(2) Next, as shown in FIG. 8B, the hollow member 14 is moved toward the proximal end of the bundle of wire-like members 12 to increase the outer diameter of the expanded outer configuration of the bundle of wire-like members 12 at the distal end (the state shown in FIG. 6), thereby expanding the portion of the blood vessel 200 around the bundle of wire-like members 12.

(3) Thereafter, the bundle of wire-like members 12 is brought closer to the clip ring 60 (or the clip ring 60 is brought closer to the bundle of wire-like members 12) to move the clip ring 60 to a position inside the bundle of wire-like members 12 increased in diameter. A portion of the blood vessel 200 including the end of the same is thereby turned inside out to form a turned portion 210, with which the periphery of the clipping 60 is covered, as shown in FIG. 8C. The bundle of wire-like members 12 is then removed from the blood vessel 200 to complete the extroverting operation.

The blood vessel extroverting instrument of the present invention has been described with respect to the illustrated embodiments. However, the present invention is not limited to the described embodiment. Each component constituting the blood vessel extroverting instrument can be replaced with a component of a different construction capable of performing the same function.

For example, the mechanism for changing the diameter (size) of the ring portion is not limited to those having the illustrated constructions, and may be replaced by a mechanism of a forcipate (scissor-like) structure, a mechanism of an endoscope forcipate structure, or any of other mechanisms, such as a rotary mechanism, a link mechanism, a cam mechanism, and a gear mechanism, capable of transmitting an operating force.

The ring portion may be arranged in such a manner that it is in the large-diameter state when the blood vessel extroverting instrument is in the unrestrained state, and its diameter is reduced when an external force (operating force) is applied to the instrument.

The shape and structure of the ring portion are not limited to those in the illustrated embodiments as long as the ring portion has a generally circular configuration. "Generally circular configuration" denotes a category including a C-shape, an elliptical shape, a looped shape, a coiled shape, polygonal shapes, and combinations of these shapes.

While the structures having supporting portions have been described, the arrangement may alternatively be taken such that proximal ends of wire-like members in a bundle are combined to form a portion to be used as a supporting portion and as a grip portion.

Further, the shape and structure of each of the supporting portion and the hollow member are not limited to those in the illustrated embodiments. For example, a member having a polygonal cross-sectional configuration may be used preferably.

What is claimed is:

1. A blood vessel extroverting instrument used to turn an end of a blood vessel inside out, said instrument comprising:
    a contact portion to be brought into contact with the end of the blood vessel;
    a supporting portion on which said contact portion is supported; and
    an operating mechanism for increasing and reducing the diameter of said contact portion,
    wherein said contact portion comprises a ring portion formed of a wire-like member in the form of a substantially circular ring, said ring portion being supported on said supporting portion, and operation of the operating mechanism increasing and reducing the diameter of said ring portion;
    said supporting portion comprises a pair of arms each having a distal end, said ring portion being connected to the distal end of each arm, and the diameter of said ring portion being changeable by changing the distance between the distal ends of said pair of arms; and
    said ring portion is insertable into the blood vessel through the opening of the end of the blood vessel while being maintained in a reduced diameter state, and the diameter of said ring portion is thereafter adapted to be increased, whereby
    the end of the blood vessel is expanded and/or reversed by operating said operating mechanism.

2. A blood vessel extroverting instrument according to claim 1, wherein said contact portion is made of an elastic material or a superelastic material.

3. A blood vessel extroverting instrument according to claim 1, further comprising a regulatory means for regulating said operating mechanism.

4. A blood vessel extroverting instrument according to claim 3, wherein said regulatory means includes an adjustment means capable of position adjustment.

5. A blood vessel extroverting instrument according to claim 1, wherein said wire-like member or said pair of arms include intermediate portions intersecting each other.

6. A blood vessel extroverting instrument according to claim 1, wherein the diameter of said ring portion is changed by changing the length of said wire-like member forming said ring portion.

7. A blood vessel extroverting instrument according to claim 1, wherein said contact portion is in the state of having its diameter reduced when said supporting portion is in an unrestrained state, and the diameter of said contact portion is increased when said supported portion is in an urged state.

8. A set of a blood vessel extroverting instrument according to claim 2 and a clip ring capable of being fitted around a blood vessel.

9. The blood vessel extroverting instrument of claim 1, wherein said member forming the substantially circular ring is a one-piece member.

10. A blood vessel extroverting instrument used to turn an end of a blood vessel inside out, the instrument comprising:
    a contact portion to be brought into contact with an inside of the end of the blood vessel;
    the contact portion being supported by a supporting portion and defining an outer circumference that is adjustable;
    the supporting portion comprising an operating mechanism for changing the outer circumference defined by the contact portion between a relatively smaller outer circumference permitting the contact portion to be introduced into the inside of the end of the blood vessel and a relatively larger outer circumference after the contact portion has been introduced into the inside of the blood vessel to permit the blood vessel to be turned inside out;
    wherein said contact portion comprises a ring portion formed of a wire-like member in the form of a substantially annular ring, said ring portion being supported on said supporting portion, and operation of the operating mechanism increasing and reducing the outer circumference of said ring portion; and said supporting portion comprising a pair of arms each having a distal end, said ring portion being connected to the distal end of each arm, and the outer circumference of said ring portion being changeable by changing the distance between the distal ends of said pair of arms.

11. A set of a blood vessel extroverting instrument according to claim 10 and a clip ring capable of being fitted around a blood vessel.

12. The blood vessel extroverting instrument of claim 10, wherein said member forming the substantially annular ring is a single member.

13. A blood vessel extroverting instrument used to turn an end of a blood vessel inside out, the instrument comprising:
   an annular ring portion formed of a wire-like member, said ring portion being positionable inside the blood vessel and adapted to be brought into contact with an inside of the end of the blood vessel, said ring portion possessing an outer circumference that is adjustable;
   a supporting portion on which said ring portion is supported, said supporting portion comprising a tubular insertion portion; and
   wherein a portion of the wire-like member which forms the ring portion extends into the tubular portion and is connected to a slider portion which is movable relative to the insertion portion to adjust the outer circumference of the ring portion between a relatively smaller outer circumference permitting the ring portion to be introduced into the inside of the end of the blood vessel and a relatively larger outer circumference after the ring portion has been introduced into the inside of the blood vessel to permit the blood vessel to be turned inside out.

14. The blood vessel extroverting instrument of claim 13, wherein at least a portion of the ring portion is positioned outside the tubular portion both before and during introduction of the ring portion into the inside of the blood vessel.

15. A method of turning an end of a blood vessel inside out comprising:
   positioning an annular ring portion inside the end portion of the blood vessel while the ring portion is in a relatively smaller outer circumference state, the ring portion being expandable from the relatively smaller outer circumference state to a relatively larger outer circumference state;
   expanding the outer circumference of the ring portion to the relatively larger outer circumference state while the ring portion is positioned inside the end portion of the blood vessel to outwardly expand at least a part of the end portion of the blood vessel; and
   turning the end portion of the blood vessel inside out.

* * * * *

UNITED STATES PATENT AND TRADEMARK OFFICE
CERTIFICATE OF CORRECTION

| | | |
|---|---|---|
| PATENT NO. | : 6,979,337 B2 | Page 1 of 1 |
| APPLICATION NO. | : 09/993633 | |
| DATED | : December 27, 2005 | |
| INVENTOR(S) | : Yukitoshi Kato | |

It is certified that error appears in the above-identified patent and that said Letters Patent is hereby corrected as shown below:

Column 14, claim 8, line 41, change "2" to --1--.

Signed and Sealed this

Twenty-sixth Day of June, 2007

JON W. DUDAS
*Director of the United States Patent and Trademark Office*